(12) United States Patent
Orenga et al.

(10) Patent No.: US 8,741,597 B2
(45) Date of Patent: Jun. 3, 2014

(54) **REACTION MEDIUM FOR METHICILLIN-RESISTANT *STAPHYLOCOCCUS AUREUS***

(75) Inventors: Sylvain Orenga, Neuville sur Ain (FR); Denis Robichon, Blyes (FR)

(73) Assignee: Biomérieux, Marcy l'Etoile (FR)

( * ) Notice: Subject to any disclaimer, the term of this patent is extended or adjusted under 35 U.S.C. 154(b) by 0 days.

(21) Appl. No.: 13/062,849

(22) PCT Filed: Oct. 7, 2009

(86) PCT No.: PCT/FR2009/051909
§ 371 (c)(1),
(2), (4) Date: Mar. 8, 2011

(87) PCT Pub. No.: WO2010/040952
PCT Pub. Date: Apr. 15, 2010

(65) Prior Publication Data
US 2011/0165614 A1    Jul. 7, 2011

(30) Foreign Application Priority Data

Oct. 8, 2008    (FR) ..................................... 08 56815

(51) Int. Cl.
*C12Q 1/14*    (2006.01)
(52) U.S. Cl.
USPC ................... 435/36; 435/18; 435/19; 435/21; 435/24; 435/34
(58) Field of Classification Search
USPC ............................. 435/18, 19, 21, 24, 34, 36
See application file for complete search history.

(56) References Cited

U.S. PATENT DOCUMENTS

| 6,548,268 | B1 | 4/2003 | Rambach |
| 2003/0235879 | A1 | 12/2003 | Sandberg et al. |
| 2004/0121404 | A1 | 6/2004 | Cotte et al. |
| 2004/0235012 | A1* | 11/2004 | Hammann et al. ................ 435/6 |
| 2007/0292908 | A1 | 12/2007 | Robichon |
| 2008/0145879 | A1 | 6/2008 | Orenga et al. |
| 2009/0017481 | A1 | 1/2009 | Orenga et al. |

FOREIGN PATENT DOCUMENTS

| EP | 0 887 424 A2 | 12/1998 |
| FR | 2 790 765 A | 9/2000 |
| FR | 2 881 755 A1 | 8/2006 |
| JP | A-06-217760 | 8/1994 |
| JP | A-07-000181 | 1/1995 |
| WO | WO 02/079486 A2 | 10/2002 |
| WO | WO 2004/027086 A1 | 4/2004 |
| WO | WO 2004/063391 A1 | 7/2004 |
| WO | WO 2007/096639 A2 | 8/2007 |
| WO | WO 2007/099254 A2 | 9/2007 |
| WO | WO 2010/040952 A2 | 4/2010 |

OTHER PUBLICATIONS

Laustriat, Gilbert et al. Influence of 3-substitution on excited state properties of indole in aqueous solutions. Excited states in organic chemistry and biochemistry. Jerusalem Symposia on Quantum Chemistry and Biochemistry. Editors: Pullman and Goldblum. Mar. 1977 (Published by D. Reidel Publishing Company: Dordrecht-Holland).pp. 151-162.*
Perry et al.; "Development and Evaluation of a Chromogenic Agar Medium for Methicillin-Resistant *Staphylococcus aureus*;" *Journal of Clinical Microbiology*; Oct. 2004; pp. 4519-4523; vol. 42, No. 10; American Society for Microbiology.
Athanasopoulos et al.; "Comparison of three selective chromogenic media for Methicillin-Resistant *Staphylococcus aureus* detection;" *Pathologie Biologie*; 2007; pp. 366-369; vol. 55; Elsevier Masson SAS (with Abstract).
Gaillot et al.; "Evaluation of CHROMagar *Staph. aureus*, a New Chromogenic Medium, for Isolation and Presumptive Identification of *Staphylococcus aureus* from Human Clinical Specimens;" *Journal of Clinical Microbiology*; Apr. 2000; pp. 1587-1591; vol. 38, No. 4; American Society for Microbiology.
Wertheim et al.; "Improved Detection of Methicillin Resistant *Staphylococcus aureus* Using Phenyl Mannitol Broth Containing Aztreonam and Ceftizoxime;" *Journal of Clinical Microbiology*; Jul. 2001; pp. 2660-2662; vol. 39, No. 7; American Society for Microbiology.
Brown et al.; "Guidelines for the laboratory diagnosis and susceptibility testing of methicillin-resistant *Staphylococcus aureus* (MRSA);" *Journal of Antimicrobial Chemotherapy*; 2005; pp. 1000-1018; vol. 56; Oxford University Press.
International Search Report dated Jun. 1, 2010 in International Application No. PCT/FR2009/051909 (with translation).
Written Opinion of the International Searching Authority dated Jun. 1, 2010 in International Application No. PCT/FR2009/051909 (with translation).
Feb. 4, 2011 International Search Report issued in International Patent Application No. PCT/FR2010/051705 (with translation).
Feb. 4, 2011 Written Opinion issued in International Patent Application No. PCT/FR2010/051705 (with translation).
Mar. 9, 2010 International Search Report for International Patent Application No. PCT/FR2009/051908 (with translation).
Mar. 9, 2010 Written Opinion for International Patent Application No. PCT/FR2009/051908 (with translation).
Manafi et al., "Fluorogenic and Chromogenic Substrates Used in Bacterial Diagnostics," Microbiological Reviews, vol. 55, No. 3, Sep. 1991, pp. 335-348.
Ito, K. et al, "Pharmacokinetics of Cephem Antibiotics in Exudate of Pelvic Retroperitoneal Space After Radical Hysterectomy and Pelvic Lymphadenectomy", Antimicrobial Agents and Chemotherapy, 1990, vol. 34(6), pp. 1160-1164.
Lo, J. et al, "Vancomycin and Amikacin in Cell Cultures for Virus Isolation", Pathology: The Journal of the Royal College of Pathologists of Australasia, 1996, vol. 28(4), pp. 366-369.
Guay, Dr., "Cedinir: An Advanced-Generation, Broad-spectrum Oral Cephalosporin", Clinical Therapeutics, 2002, vol. 24(4), pp. 473-489.
Velasco et al., "Evaluation of different methods for detecting methicillin (oxacillin) resistance in *Staphylococcus aureus*," Journal of Antimicrobial Chemotherapy, Feb. 18, 2005, pp. 379-382, vol. 55, The British Society for Antimicrobial Chemotherapy 2005.

(Continued)

*Primary Examiner* — Susan Hanley
*Assistant Examiner* — Nghi Nguyen
(74) *Attorney, Agent, or Firm* — Oliff PLC

(57) ABSTRACT

A reaction medium for detecting and/or identifying *Staphylococcus aureus* bacteria, comprising a combination of two enzymatic substrates for alpha-glucosidase.

10 Claims, No Drawings

(56) References Cited

OTHER PUBLICATIONS

Kluytmans et al., "Performance of CHROMagar Selective Medium and Oxacillin Resistance Screening Agar Base for Identifying *Staphylococcus aureus* and Detecting Methicillin Resistance," Journal of Clinical Microbiology, Jul. 2002, vol. 40, No. 7, pp. 2480-2482, American Society for Microbiology.

Merlino et al., "Detection and expression of methicillin/oxacillin resistance in multidrug-resistant and non-multidrug-resistant *Staphylococcus aureus* in Central Sydney, Australia," Journal of Antimicrobial Chemotherapy, 2002, vol. 49, pp. 793-801, The British Society for Antimicrobial Chemotherapy.

May 14, 2012 Office Action issued in U.S. Appl. No. 13/062,768.

Jun. 21, 2012 Office Action issued in U.S. Appl. No. 12/839,946.

U.S. Appl. No. 12/839,946 in the name of Roche et al., filed Jul. 20, 2010.

U.S. Appl. No. 13/062,768 in the name of Orenga et al., filed Mar. 8, 2012.

Jan. 7, 2013 Office Action issued in U.S. Appl. No. 12/839,946.

\* cited by examiner

REACTION MEDIUM FOR METHICILLIN-RESISTANT STAPHYLOCOCCUS AUREUS

The present invention relates to a culture medium for detecting *Staphylococcus aureus* bacteria. The invention also relates to the use of this medium and to a method for identifying *S. aureus* bacteria.

In 2008, the *Staphylococcus* genus included forty-one species and twenty-four sub-species, at least seventeen of which have been found in humans. Most of these species are opportunistic pathogens in humans exhibiting a high risk in the event of a skin injury due to trauma or due to direct implantation of a medical product. Moreover, the *S. aureus* species is a bacterium often found in patients who have to receive hospital care involving devices such as syringes or catheters. There is therefore a great advantage in detecting the presence of this pathogenic bacterium, which is increasingly implicated in nosocomial diseases.

Among the staphylococci, *S. aureus* is unquestionably the most virulent species, since it produces a large number of toxins and extracellular enzymes. It can be responsible for numerous and varied pathologies, ranging from simple whitlow to the most severe infections such as septicaemia, endocarditis, pneumopathies or osteoarticular infections, for which the prognosis may not be very optimistic.

In addition, only five species: *S. aureus, Staphylococcus epidermidis, Staphylococcus haemolyticus, Staphylococcus saprophyticus* and *Staphylococcus hominis* represent at least 1% of the pathogenic strains isolated in clinical centres, and these five represent more than 98% of the staphylococcal strains most commonly encountered. The other species are rarely encountered and are not very pathogenic.

In bacteriology, it is conventional practice to contrast the *S. aureus* species, characterized by the production of a coagulase, with the other, "coagulase-negative", species.

The conventional methods for distinguishing *S. aureus* from *Staphylococcus* non aureus are based on the search for free coagulase and for DNase and on obtaining agglutination on latex, aimed at demonstrating the presence of fibrinogen affinity factor, of protein A and of capsular antigens.

One should be aware that other, potentially pathogenic, staphylococcal species are capable of expressing a coagulase.

The coagulase-positive species are the following: *S. aureus, Staphylococcus intermedius, Staphylococcus hyicus, Staphylococcus delphinis, Staphylococcus lutrae* and *Staphylococcus schleiferi*.

Culture techniques on selective media exist for making it possible to evaluate the presence of *S. aureus*. The media involved are the following:

The high-salt Chapman medium (containing 75% of NaCl) is generally selective for *S. aureus* and staphylococci which hydrolyse mannitol. These bacteria cause the medium to change from red to yellow. Certain microorganisms and the group *D enterococci*, in particular, can produce the same reaction on the medium; it is therefore then necessary to verify the catalase (negative for streptococci).

The Baird-Parker egg-yoke medium (containing potassium Tellurite and lithium chloride as selective agents) is used for isolating and counting coagulase-positive staphylococci in food products and makes it possible to demonstrate lecithinase activity. On this medium, colonies of *S. aureus* and of other coagulase-positive species appear with a black centre surrounded by an opaque halo. Other microorganisms can develop on this medium. These are principally the following groups:

Gram+cocci: of the *Enterococcus* and *Listeria* genera,
Gram−bacilli: of the *Proteus* and *Pseudomonas* genera.

The Baird-Parker medium+RPF (rabbit plasma+bovine fibrinogen) is used for isolating and counting coagulase-positive staphylococci in food products, reference medium in accordance with ISO standard 6888-1 and 6888-2, and makes it possible to demonstrate coagulase activity. On this medium, the *S. aureus* colonies and other coagulase-positive species appear with a black centre surrounded by an opaque halo.

In fact, the revealing of *S. aureus* which uses the Chapman high-salt medium technique lacks sensitivity (ability to reveal the species being sought when the latter is present in a small amount in a biological test sample) and especially specificity (ability to detect the species being sought in the biological test sample containing other species).

Similarly, the revealing of *S. aureus* which uses the Baird-Parker egg-yoke medium technique lacks sensitivity and specificity. Thus, some strains that do not belong to the species *S. aureus*, in particular *Staphylococcus schleiferi* and *Staphylococcus saprophyticus*, can also give colonies surrounded by a lighter halo. It may also be that certain strains of *S. aureus* do not express the enzymatic activity being sought or do not develop on the medium, since they may be present in too small an amount in the biological samples and/or may be inhibited by components of the medium that are too selective.

In the case of the Baird-Parker+RPF medium, a certain number of drawbacks are generally observed. Firstly, there are difficulties in terms of reading and sensitivity; false negatives can potentially appear due to the fact that certain strains of *S. aureus* do not develop on this medium or exhibit a very weak and late coagulase, leading to the assumption of the presence of coagulase-negative staphylococci. Furthermore, false-negative results may also be observed owing to matricial interferences; specifically, for counting low levels of *S. aureus* contamination, a minimum dilution of the sample is carried out (1/10), which causes a difficulty in reading the halo due to the presence of matrix compounds (e.g. samples of milk and/or milk products: white colour of casein masking the halo that reveals coagulase). The Baird-Parker+RPF medium requires the combination of a source of thrombin and of a source of plasminogen. These are obtained from animal blood, which poses problems of reliability of supply (quality, quantity, etc.). In addition, it is not possible to read a halo in a broth (liquid medium), and the contrast between the halo and the medium may be low. Finally, in the case of confluent colonies, it is difficult to determine those which produce the halo compared with those which do not produce it.

Secondly, problems of specificity may also exist: in the presence of an abundant secondary flora (such as, for example, *Bacillus* spp), false-positive results may appear with this type of medium. This is, for example, the case when counting *S. aureus* in certain meat products (dry sausage) and dairy products (cheeses of the Munster type) in which *Staphylococcus xylosus* is used as a ferment. Thus, black colonies surrounded by a halo appear on the Baird-Parker+RPF medium, these being colonies which are normally characteristic of *S. aureus* on this medium, but which are in reality the consequence of contiguous growth of *S. xylosus* strains (producing black colonies without a halo) and of certain strains of *Bacillus* which have a coagulase (generating a halo), on agar.

It is therefore understood that this revealing with Baird-Parker, Baird-Parker+RPF and Chapman media gives only a presumptive diagnosis and requires other confirmation tests. However, the additional handling, required for identifying *S.*

*aureus*, increases the duration and the cost of the analyses. They require a multitude of reagents and the involvement of qualified staff.

It is also possible to use media based on enzymatic substrates.

An article: "Evaluation of CHROMagar *Staph. aureus*, a new chromogenic medium, for isolation and presumptive identification of *S. aureus* from human clinical specimens." by O. Gaillot et al. 2000. J. Clin. Microbial. 38, 4, 1587-1591, describes and evaluates a chromogenic culture medium, CHROMagar (registered trade mark) *Staph. aureus*, for isolating staphylococci and identifying *S. aureus* using chromogenic substrates which give a mauve colouration of the latter species. The other species of the same genus are then detected through being blue in colour or colourless, in theory. β-glucosidase, β-glucuronidase, β-galactosidase and phosphatase activities are essentially used, along with an inhibitor, Deferoxamine, which makes it possible to distinguish between *S. aureus* and *S. epidermidis*. However, the distinction between *S. aureus* and *S. epidermidis* is difficult, since the two species produce colonies of the same colour on the CHROMagar (registered trade mark) medium. This is due to the lack of specificity of the phosphatase substrates, which are positive for *S. aureus* and *S. epidermidis*, and to the fact that the inhibition of the latter by Deferoxamine is only partial.

Mention may also be made of application WO 02079486, which describes the use of an α-glucoside substrate for identifying the various staphylococcal species, which may be in combination with a substrate for another enzymatic activity. However, under certain conditions, such as, for example, with strains having a weak α-glucosidase activity and present in small amounts (2 to 50 colony forming units), the detection of the activity may be late and require more than 24 hours of incubation.

The invention proposes to solve the gaps in the prior art by providing a new, sensitive, specific and rapid culture medium for isolating and identifying *S. aureus*.

Before proceeding further, the following definitions, which are in no way limiting, will make it possible to understand the invention more clearly.

For the purpose of the present invention, the term reaction medium is intended to mean a medium comprising all the elements necessary for the survival and/or growth of microorganisms, such as *S. aureus*.

This reaction medium may either serve as a revealing medium only, or as a culture and revealing medium. In the first case, the microorganisms are cultured before inoculation, and in the second case, the reaction medium also constitutes the culture medium.

The reaction medium may be solid, semi-solid or liquid. The term "solid medium" is intended to mean, for example, a gelled medium. Preferably, the medium according to the invention is a gelled medium, Agar is the conventional gelling agent in microbiology for culturing microorganisms, but it is possible to use gelatine or agarose. A certain number of preparations are commercially available, for instance Colombia agar, Trypticase-soy agar, Mac Conkey agar, Sabouraud agar, or more generally those described in the Handbook of Microbiological Media (CRC Press).

The reaction medium according to the invention may contain other possible additives, for instance: peptones, one or more growth factors, carbohydrates, one or more selective agents, buffer solutions, one or more gelling agents, etc. This reaction medium may be in the form of a liquid or of a gel that is ready-to-use, i.e. ready for inoculation in a tube or flask or on a Petri dish. When this medium is provided in the form of a gel in a flask, the medium is preferably regenerated (subjected to 100° C.) before being poured into a Petri dish.

Preferably, the medium according to the invention is a selective medium, i.e. a medium comprising inhibitors which favour the growth of *Staphylococcus aureus* bacteria. Mention may in particular be made of lithium chloride (LiCl), sodium azide ($NaN_3$), colistin, amphotericin, aztreonam, colimycin, sodium chloride (NaCl), deferoxamine, and the vibriostatic compound O/129.

This medium may also be suitable for the detection of Methicillin-resistant *S. aureus*(MRSA), and may comprise one or more antibiotics, against which MRSAs are resistant, such as a cephalosporin or a carbapenem, preferably selected from:

a first-generation cephalosporin, such as Cefalexin, Cefaloridine, Cefalotin, Cefazolin, Cefadroxil, Cefazedone, Cefatrizine, Cefapirin, Cefradine, Cefacetrile, Cefrodaxine, Ceftezole;

a second-generation cephalosporin, such as Cefoxitin, Cefuroxime, Cefamandole, Cefaclor, Cefotetan, Cefonicide, Cefotiam, Loracarbef, Cefmetazole, Cefprozil, Ceforanide;

a third-generation cephalosporin, such as Cefotaxime, Ceftazidime, Cefsulodine, Ceftriaxone, Cefmenoxime, Latamoxef, Ceftizoxime, Cefixime, Cefodizime, Cefetamet, Cefpiramide, Cefoperazone, Cefpodoxime, Ceftibuten, Cefdinir, Cefditoren, Ceftriaxone, Cefoperazone;

a fourth-generation cephalosporin, such as Cefepime, Cefpirome;

Meropenem, Ertapenem, Imipenem.

For the purposes of the present invention, the substrate for an enzymatic activity (or enzymatic substrate) is selected from any substrate that can be hydrolyzed to give a product which enables the direct or indirect detection of an alpha-glucosidase enzymatic activity.

It may be a natural or synthetic substrate. The metabolism of the substrate causes a variation in the physicochemical properties of the reaction medium or of the cells of organisms. This variation can be detected by physicochemical methods, in particular optical methods, visually by the operator or using spectrometric, electrical, magnetic, etc., instruments. Preferably, it is a variation in the optical properties, such as a modification of absorption, of fluorescence or of luminescence.

As a chromogenic substrate, mention may in particular be made of substrates based on indoxyl, flavone, alizarine, naphtolbenzein, nitrophenol, naphtol, catechol, hydroxyquinoline or coumarin. Preferably, the substrate(s) used in the present invention is (are) indoxyl-based.

As a fluorescent substrate, mention may in particular be made of substrates based on umbelliferone or on coumarin, based on resorufin, phenoxazine, naphtol, naphthylamine, or 2'-hydroxyphenyl-heterocycle or else based on fluorescein.

As a substrate for alpha-glucosidase enzymatic activity, mention may more particularly be made of the substrates 5-bromo-6-chloro-3-indoxyl-alpha-glucoside; dihydroxyflavone-alpha-glucoside; 3,4-cyclohexenoesculetin-alpha-glucoside; 8-hydroxyquinoline-alpha-glucoside; 5-bromo-4-chloro-3-indoxyl-alpha-glucoside; 5-bromo-4-chloro-3-indoxyl-N-methyl-alpha-glucoside; 6-chloro-3-indoxyl-alpha-glucoside; 5-bromo-3-indoxyl-alpha-glucoside; 5-iodo-3-indoxyl-alpha-glucoside; 6-fluoro-3-indoxyl-alpha-glucoside; alizarine-alpha-glucoside; nitrophenyl-alpha-glucoside; 4-methylumbelliferyl-alpha-glucoside; naphtholbenzein-alpha-glucoside; indoxyl-N-methyl-alphaglucoside; naphthyl-alpha-glucoside; aminophenyl-alpha-glucoside; dichloroaminophenyl-alpha-glucoside; resorufin-alpha-glucoside.

Preferably, the substrate used in the present invention is 5-bromo-4-chloro-3-indoxyl-alpha-glucoside in combination with 5-bromo-4-chloro-3-indoxyl-N-methyl-alpha-glucoside.

The substrates of the invention can be used in a wide pH range, in particular between pH 5.5 and 10, preferably between pH 6.5 and 10.

The concentration of substrate is preferably between 0.01 and 2 WI, even more preferably between 0.02 and 0.2 g/l, and is advantageously 0.1 WI. This is because, at this concentration of substrate, a better colouration contrast is obtained.

The term biological sample is intended to mean a clinical sample, derived from a bronchial, tracheal or pulmonary aspiration sample or a pleural fluid sample, from broncho-alveolar lavage, from expectorations, from blood or from a lung biopsy, from joint fluid or pericardial fluid, biological fluid or a food sample, derived from any type of food. This sample may thus be liquid or solid and mention may be made, in a nonlimiting manner, of a clinical sample from blood, plasma, urine or faeces, or from samples taken from the nose, from the perineum, from the throat, from the skin, from wounds or from cerebrospinal fluid, or a food sample.

In this respect, the invention relates to a reaction medium for detecting and/or identifying *S. aureus* bacteria, comprising a combination of two enzymatic substrates for alpha-glucosidase.

According to one preferred embodiment of the invention, one of the two substrates is an indoxyl-alpha-glucoside substrate, preferably 5-bromo-4-chloro-3-indoxyl-N-methyl-alpha-glucoside (X—N-methyl-alpha-glucoside) or 5-bromo-4-chloro-3-indoxyl-alpha-glucoside (X-alpha-glucoside).

Preferably said indoxyl-alpha-glucoside substrate is present in the medium at a concentration of between 0.01 and 2 g/l, preferably between 0.05 and 0.3 g/l.

Preferably, said combination of two enzymatic substrates for alpha-glucosidase comprises 5-bromo-4-chloro-3-indoxyl-N-methyl-alpha-glucoside and 5-bromo-4-chloro-3-indoxyl-alpha-glucoside.

According to one preferred embodiment of the invention, said medium also comprises a mixture of inhibitors which favors the growth of *Staphylococcus aureus* bacteria, preferably lithium chloride (LiCl), sodium azide ($NaN_3$), colistin, the O/129 vibriostatic compound, Aztreonam, Amphotericin, colimycin, sodium chloride (NaCl) and Deferoxamine.

According to one preferred embodiment of the invention, the medium also comprises a mixture of inhibitors, comprising four inhibitors, which favours the growth of bacteria of the *Staphylococcus* genus, said inhibitors being LiCl, the O/129 vibriostatic compound, Aztreonam and Amphotericin.

The invention also relates to the in vitro use of a reaction medium as defined above, for isolating and identifying *S. aureus* bacteria.

Finally, the invention relates to a method for detecting and/or identifying *S. aureus* bacteria, in a biological sample, comprising:
 a) inoculating the biological sample that may contain *S. aureus* bacteria on a reaction medium as defined above;
 b) incubating;
 c) identifying the *S. aureus* colonies;
 d) identifying the MRSA colonies.

The incubation is preferably carried out at a temperature of between 30° C. and 42° C. The *S. aureus* are detected by means of a specific α-glucosidase activity which makes it possible to obtain coloured or fluorescent colonies. The other *Staphylococcus* species appear colourless or have a different colour or fluorescence from that of the *S. aureus* colonies.

The invention also relates to a reaction medium for detecting and/or identifying MRSA bacteria, comprising a combination of two enzymatic substrates for alpha-glucosidase and an antibiotic, against which the MRSAs are resistant, preferably a cephalosporin, such as Cefoxitin. This antibiotic may be in combination with another antibiotic. Such a combination is preferably selected from Cefoxitin/Cefotaxime or Cefoxitin/Ertapenem. Such a medium is particularly suitable for the detection of MRSAs.

According to one preferred embodiment of the invention, one of the two substrates is an indoxyl-alpha-glucoside substrate, preferably 5-bromo-4-chloro-3-indoxyl-N-methyl-alpha-glucoside (X—N-methyl-alpha-glucoside) or 5-bromo-4-chloro-3-indoxyl-alpha-glucoside (X-alpha-glucoside).

Preferably, said indoxyl-alpha-glucoside substrate is present in the medium at a concentration of between 0.01 and 2 g/l, preferably between 0.05 and 0.3 g/l.

Preferably, said combination of two enzymatic substrates for alpha-glucosidase comprises 5-bromo-4-chloro-3 indoxyl-N-methyl-alpha-glucoside and 5-bromo-4-chloro-3-indoxyl-alpha-glucoside.

According to one preferred embodiment of the invention, said medium also comprises a mixture of inhibitors which favours the growth of *Staphylococcus aureus* bacteria, preferably lithium chloride (LiCl), sodium azide ($NaN_3$), colistin, the O/129 vibriostatic compound, Aztreonam, Amphotericin, colimycin, sodium chloride (NaCl) and Deferoxamine.

The invention also relates to the in vitro use of a reaction medium as defined above, for isolating and identifying MRSA bacteria.

Finally, the invention relates to a method for detecting and/or identifying MRSA bacteria, in a biological sample, comprising:
 a) inoculating the biological sample that may contain MRSA bacteria on a reaction medium as defined above;
 b) incubating;
 c) identifying the MRSA colonies.

The incubation is preferably carried out at a temperature of between 30° C. and 42° C.

The MRSAs are detected by means of a specific α-glucosidase activity which makes it possible to obtain coloured or fluorescent colonies. The other species appear colourless or have a different colour or fluorescence from that of the MRSA colonies.

The following examples are given by way of illustration and are in no way limiting in nature. They will make it possible to understand the invention more clearly.

1. Preparation of the Medium According to the Invention

The media tested in the experiments hereinafter were media comprising the chromID MRSA medium (bioMérieux ref. 43 451) as basic medium, and comprising the following elements:
 Medium T: chromID MRSA control medium (ref. 43 451), comprising in particular an X—N-methyl-alpha-glucoside substrate, at a concentration of 0.1 g/l, and Cefoxitin at 4 mg/l,
 Medium S: medium T, also comprising an X-alpha-glucoside substrate, at a concentration of 25, 37, 45 or 50 mg/l.
 Medium F: medium S (X-alpha-glucoside concentration: 45 mg/l), the Cefoxitin being substituted with a Cefoxitin/Cefotaxime at the concentrations below:

| [Cefoxitin] in mg/l | 0.5 | 0.5 | 1 | 1 |
| [Cefotaxime] in mg/l | 0.5 | 1 | 0.5 | 1 |

Medium G: medium S (X-alpha-glucoside concentration: 45 mg/l), the Cefoxitin being substituted with a Cefoxitin/Ceftriaxone combination at the concentrations below:

| [Cefoxitin] in mg/l | 0.5 | 0.5 | 1 | 1 |
| [Ceftriaxone] in mg/l | 0.5 | 1 | 0.5 | 1 |

Medium H: medium S (X-alpha-glucoside concentration: 45 mg/l), the Cefoxitin being substituted with a Cefoxitin/Ertapenem combination at the concentrations below:

| [Cefoxitin] in mg/l | 0.5 | 0.5 | 0.5 | 0.5 | 0.75 | 0.75 | 0.75 | 0.75 |
| [Ertapenem] in mg/l | 0.25 | 0.5 | 0.75 | 1 | 0.25 | 0.5 | 0.75 | 1 |

Medium I: medium S (X-alpha-glucoside concentration: 45 mg/l), the Cefoxitin being substituted with a Cefoxitin/Cefpodoxime combination at the concentrations below:

| [Cefoxitin] in mg/l | 0.5 | 0.5 | 0.5 | 0.5 | 0.75 | 0.75 | 0.75 | 0.75 |
| [Cefpodoxime] in mg/l | 0.5 | 1 | 1.5 | 2 | 0.5 | 1 | 1.5 | 2 |

Medium J: medium S (X-alpha-glucoside concentration: 45 mg/l), the Cefoxitin being substituted with a Cefoxitin/Cefoperazone combination at the concentrations below:

| [Cefoxitin] in mg/l | 0.5 | 0.5 | 0.5 | 0.5 | 0.75 | 0.75 | 0.75 | 0.75 |
| [Cefoperazone] in mg/l | 0.5 | 0.75 | 1 | 1.5 | 0.5 | 0.75 | 1 | 1.5 |

Medium K: medium S (X-alpha-glucoside concentration: 45 mg/l), the Cefoxitin being substituted with a Cefoxitin/Cefotaxime combination, at the concentrations below, also comprising a mixture of inhibitors of microorganisms that do not belong to the *Staphylococcus* genus, favouring the growth of *S. aureus*.

| [Cefoxitin] in mg/l | 0.75 | 0.75 | 0.75 | 0.75 | 0.75 | 0.75 |
| [Cefotaxime] in mg/l | 0.5 | 0.55 | 0.6 | 0.65 | 0.7 | 0.75 |

2. Inoculation and Reading of Media

Various sets of bacterial strains, all derived from the Applicant's collection, suspended in physiological saline, were inoculated so as to give isolated colonies on the medium. The dishes were incubated at 37° C. for 48 hours. The colonies formed were examined visually after 18 h or 24 hours of incubation. The colouration intensity was also observed according to a scale of 0 to 4 (0: no colouration, 4: very intense colouration).

The strains detected correspond to the strains forming coloured colonies on the medium.

3. Results:

3.1 Medium for Detecting Mrsas, Comprising Two Alpha-Glucosidase Substrates

The results obtained during the use of one or two alpha-glucosidase substrates are given in table 1.

TABLE 1

Intensity of colouration of the colonies during the use of two alpha-glucosidase substrates

| Strains | Incubation | Medium T Intensity of green colouration | Medium S [X α Glu] = 25 mg/l Intensity of green colouration | Medium [X α Glu] = 37 mg/l Intensity of green colouration | Medium [X α Glu] = 50 mg/l Intensity of green colouration |
|---|---|---|---|---|---|
| MRSA | 18 h | 2 | 2 | 2.5 | 3 |
|  | 24 h | 2 | 2 | 3 | 3 |
|  | >40 h | 2 | 2.5 | 3 | 3 |
| MRSA | 18 h | 0 | 0 | 0 | 0 |
|  | 24 h | 2 | 2 | 2.5 | 3 |
|  | >40 h | 3 | 3 | 4 | 4 |
| MRSA | 18 h | 1.5 | 1.5 | 2 | 3 |
|  | 24 h | 2 | 2 | 4 | 4 |
|  | >40 h | 2 | 3 | 4 | 4 |
| MRSA | 18 h | 2 | 2 | 3 | 3 |
|  | 24 h | 2 | 2 | 4 | 4 |
|  | >40 h | 2.5 | 2.5 | 4 | 4 |
| MRSA | 18 h | 0.5 | 0.5 | 0 | 0 |
|  | 24 h | 1 | 0.5 | 1.5 | 2.5 |
|  | >40 h | 2.5 | 3 | 4 | 4 |
| MRSA | 18 h | 2 | 2 | 2.5 | 3 |
|  | 24 h | 2.5 | 2.5 | 2.5 | 2.5 |
|  | >40 h | 2.5 | 3 | 4 | 4 |
| MRSA | 18 h | 0 | 0 | 0 | 0 |
|  | 24 h | 1 | 1 | 3 | 4 |
|  | >40 h | 2 | 3 | 4 | 4 |
| MRSA | 18 h | 0 | 0 | 0 | 0 |
|  | 24 h | 0 | 0 | 0 | 0 |
|  | >40 h | 3 | 3 | 4 | 4 |

TABLE 1-continued

Intensity of colouration of the colonies during the use of two alpha-glucosidase substrates

| Strains | Incubation | Medium T Intensity of green colouration | Medium S [X α Glu] = 25 mg/l Intensity of green colouration | Medium [X α Glu] = 37 mg/l Intensity of green colouration | Medium [X α Glu] = 50 mg/l Intensity of green colouration |
|---|---|---|---|---|---|
| MRSA | 18 h | 1.5 | 1.5 | 3 | 2.5 |
|  | 24 h | 2 | 2 | 4 | 4 |
|  | >40 h | 2.5 | 3 | 4 | 4 |
| MRSA | 18 h | 0 | 0 | 0 | 0 |
|  | 24 h | 0 | 0 | 2 | 3 |
|  | >40 h | 2.5 | 3 | 4 | 4 |

The addition of a second alpha-glucosidase substrate makes it possible to strongly intensify the colouration of the colonies, thus making it possible to achieve better pinpointing of the MRSA colonies.

3.2—Medium for Detecting MRSAs, Comprising Two Alpha-Glucosidase Substrates and a Combination of Antibiotics Selected from the Pairs Cefoxitin/Ceftriaxone, Cefoxitin/Cefotaxime, Cefoxitin/Ertapenem, Cefoxitin/Cefoperazone or Cefoxitin/Cefpodoxime The results obtained when combinations of antibiotics were used are given in table 2.

TABLE 2

Detection of MRSA colonies when a combination of antibiotics was used (detection expressed as number of strains detected per number of total strains)

| Medium | | T | | F | | | T | | G | | |
|---|---|---|---|---|---|---|---|---|---|---|---|
| Antibiotic 1 | | Cefoxitin | | Cefoxitin | | | Cefoxitin | | Cefoxitin | | |
| Concentration Antibiotic 1 (mg/l) | | 4 | 0.5 | 1 | 0.5 | 1 | 4 | 0.5 | 1 | 0.5 | 1 |
| Antibiotic 2 | | None | | Cefotaxime | | | None | | Ceftriaxone | | |
| Concentration Antibiotic 2 (mg/l) | | 0 | 0.5 | 0.5 | 1 | 1 | 0 | 0.5 | 0.5 | 1 | 1 |
| MRSA | Reading 18 h | 6/10 | 9/10 | 8/10 | 6/10 | 5/10 | 6/10 | 9/10 | 8/10 | 9/10 | 8/10 |
|  | Reading 24 h | 8/10 | 10/10 | 8/10 | 6/10 | 6/10 | 8/10 | 10/10 | 10/10 | 10/10 | 8/10 |
| MSSA | Reading 18 h | — | 4/10 | 1/10 | 1/10 | — | — | 6/10 | 4/10 | 4/10 | 3/10 |
|  | Reading 24 h | — | 5/10 | 2/10 | 1/10 | — | — | 6/10 | 5/10 | 4/10 | 4/10 |

| Medium | | T | | | | | H | | | | |
|---|---|---|---|---|---|---|---|---|---|---|---|
| Antibiotic 1 | | Cefoxitin | | | | | Cefoxitin | | | | |
| Concentration Antibiotic 1 (mg/l) | | 4 | 0 | 0.5 | 0.5 | 0.5 | 0.5 | 0.75 | 0.75 | 0.75 | 0.75 |
| Antibiotic 2 | | None | | | | | Ertapenem | | | | |
| Concentration Antibiotic 2 (mg/l) | | 0 | 1 | 0.25 | 0.5 | 0.75 | 1 | 0.25 | 0.5 | 0.75 | 1 |
| MRSA | Reading 18 h | 6/10 | 7/10 | 8/10 | 7/10 | 7/10 | 6/10 | 7/10 | 7/10 | 7/10 | 2/10 |
|  | Reading 24 h | 6/10 | 8/10 | 8/10 | 8/10 | 8/10 | 7/10 | 8/10 | 8/10 | 8/10 | 4/10 |
| MSSA | Reading 18 h | — | 3/10 | 9/10 | 6/10 | 2/10 | — | 7/10 | 3/10 | 10/10 | — |
|  | Reading 24 h | — | 5/10 | 9/10 | 8/10 | 5/10 | — | 10/10 | 6/10 | 10/10 | — |

| Medium | | T | | | | | I | | | | |
|---|---|---|---|---|---|---|---|---|---|---|---|
| Antibiotic 1 | | Cefoxitin | | | | | Cefoxitin | | | | |
| Concentration Antibiotic 1 (mg/l) | | 4 | 0 | 0.5 | 0.5 | 0.5 | 0.5 | 0.75 | 0.75 | 0.75 | 0.75 |
| Antibiotic 2 | | None | | | | | Cefpodoxime | | | | |
| Concentration Antibiotic 2 (mg/l) | | 0 | 2 | 0.5 | 1 | 1.5 | 2 | 0.5 | 1 | 1.5 | 2 |
| MRSA | Reading 18 h | 5/10 | 5/10 | 8/10 | 5/10 | 5/10 | 1/10 | 6/10 | 5/10 | 4/10 | 1/10 |
|  | Reading 24 h | 5/10 | 5/10 | 8/10 | 5/10 | 5/10 | 5/10 | 7/10 | 5/10 | 5/10 | 3/10 |
| MSSA | Reading 18 h | — | 4/10 | 6/10 | — | — | — | 2/10 | — | — | — |
|  | Reading 24 h | — | 4/10 | 7/10 | 1/10 | — | — | 5/10 | — | — | — |

TABLE 2-continued

Detection of MRSA colonies when a combination of antibiotics was used (detection expressed as number of strains detected per number of total strains)

| | Medium | T | J | | | | | | | | |
|---|---|---|---|---|---|---|---|---|---|---|---|
| | Antibiotic 1 | | Cefoxitin | | | | | | | | |
| | Concentration Antibiotic 1 (mg/l) | 4 | 0 | 0.5 | 0.5 | 0.5 | 0.5 | 0.75 | 0.75 | 0.75 | 0.75 |
| | Antibiotic 2 | None | Cefoperazone | | | | | | | | |
| | Concentration Antibiotic 2 (mg/l) | 0 | 1.5 | 0.5 | 0.75 | 1 | 1.5 | 0.5 | 0.75 | 1 | 1.5 |
| MRSA | Reading 18 h | 5/10 | 5/10 | 6/10 | 5/10 | 5/10 | 2/10 | 5/10 | 5/10 | 5/10 | 1/10 |
| | Reading 24 h | 5/10 | 7/10 | 9/10 | 5/10 | 5/10 | 4/10 | 6/10 | 6/10 | 5/10 | 2/10 |
| MSSA | Reading 18 h | — | 6/10 | 4/10 | 3/10 | 2/10 | — | 4/10 | 3/10 | 1/10 | — |
| | Reading 24 h | — | 7/10 | 5/10 | 4/10 | 3/10 | 1/10 | 4/10 | 4/10 | 2/10 | 1/10 |

Combinations of antibiotics above make it possible to obtain performance levels that are better than those of a medium with Cefoxitin alone at 4 mg/l.

3.3. Medium for Detecting MRSAs, Comprising a Cefoxitin/Cefotaxime Antibiotic Combination and a Mixture of Inhibitors Favouring the Growth of *S. Aureus*

The results obtained when combinations of antibiotics were used are given in table 3.

TABLE 3

Detection of MRSA colonies when a Cefoxitin/Cefotaxime antibiotic combination and a mixture of inhibitors were used (detection expressed as number of strains detected per number of total strains)

| | Medium | T | K | | | | | |
|---|---|---|---|---|---|---|---|---|
| | Antibiotic 1 | Cefoxitin | Cefoxitin | | | | | |
| | Concentration Antibiotic 1 (mg/l) | 4 | 0.5 | 0.55 | 0.6 | 0.65 | 0.7 | 0.75 |
| | Antibiotic 2 | None | Cefotaxime | | | | | |
| | Concentration Antibiotic 2 (mg/l) | 0 | 0.75 | 0.75 | 0.75 | 0.75 | 0.75 | 0.75 |
| MRSA | Reading 18 h | 5/10 | 5/10 | 5/10 | 5/10 | 5/10 | 5/10 | 5/10 |
| | Reading 24 h | 9/10 | 8/10 | 9/10 | 8/10 | 8/10 | 8/10 | 9/10 |
| MSSA | Reading 18 h | — | — | — | — | — | — | — |
| | Reading 24 h | — | 3/10 | 2/10 | 1/10 | — | — | — |

The Cefoxitin/Cefotaxime antibiotic combination combined with a mixture of inhibitors promoting the growth of *S. aureus* made it possible to obtain an excellent specificity and sensitivity, in particular when a Cefoxitin and a Cefotaxime concentration of 0.75 mg/l was used.

The invention claimed is:

1. A reaction medium for detecting and/or identifying Methicillin-resistant *Staphylococcus aureus* (MRSA) bacteria, comprising a combination of two different indoxyl enzymatic substrates for alpha-glucosidase and an antibiotic, against which the MRSA bacteria are resistant, wherein each indoxyl enzymatic substrate is at a concentration from 0.01 to 2 g/l, and wherein the indoxyl moiety of each indoxyl enzymatic substrate is substituted by one or two halogens.

2. The reaction medium according to claim 1, wherein the reaction medium comprises a second antibiotic, against which the MRSA bacteria are resistant.

3. The reaction medium according to claim 1, wherein said combination of two indoxyl enzymatic substrates for alpha-glucosidase comprises 5-bromo-4-chloro-3-indoxyl-N-methyl-alpha-glucoside and 5-bromo-4-chloro-3-indoxyl-alpha-glucoside.

4. The reaction medium according to claim 1, wherein the reaction medium also comprises a mixture of inhibitors which promotes the growth of *Staphylococcus aureus* bacteria.

5. A method for detecting and/or identifying MRSA bacteria, in a biological sample, comprising:
   a) inoculating the biological sample on a reaction medium according to claim 1;
   b) incubating the biological sample; and
   c) identifying MRSA colonies on the reaction medium when MRSA bacteria is present in the biological sample.

6. The reaction medium according to claim 1, wherein each indoxyl enzymatic substrate is at a concentration from 0.02 to 0.2 g/l.

7. A reaction medium for detecting and/or identifying Methicillin-resistant *Staphylococcus aureus* (MRSA) bacteria, comprising 5-bromo-4-chloro-3-indoxyl-N-methyl-alpha-glucoside at a concentration from 0.02 to 0.2 g/l, 5-bromo-4-chloro-3-indoxyl-alpha-glucoside at a concentration from 0.02 to 0.2 g/l, and an antibiotic against which the MRSA bacteria are resistant.

8. The reaction medium according to claim 7, wherein the reaction medium further comprises a second antibiotic against which the MRSA bacteria are resistant.

9. The reaction medium according to claim 7, wherein the reaction medium further comprises a mixture of inhibitors which promotes the growth of *Staphylococcus aureus* bacteria.

10. A method for detecting and/or identifying MRSA bacteria, in a biological sample, comprising:
  a) inoculating the biological sample on a reaction medium according to claim 7;
  b) incubating the biological sample; and
  c) identifying MRSA colonies on the reaction medium when MRSA bacteria is present in the biological sample.

* * * * *